United States Patent [19]

Hallgren

[11] 4,201,721
[45] May 6, 1980

[54] CATALYTIC AROMATIC CARBONATE PROCESS

[75] Inventor: John E. Hallgren, Scotia, N.Y.

[73] Assignee: General Electric Company, Schenectady, N.Y.

[21] Appl. No.: 892,509

[22] Filed: Apr. 3, 1978

Related U.S. Application Data

[63] Continuation-in-part of Ser. No. 731,494, Oct. 12, 1976, abandoned.

[51] Int. Cl.$^2$ ............................................. C07C 68/00
[52] U.S. Cl. ................................... 260/463; 528/219
[58] Field of Search ..................... 260/463, 47 XA; 528/219

[56] References Cited

U.S. PATENT DOCUMENTS

| | | | |
|---|---|---|---|
| Re. 29,338 | 9/1976 | Perrotti et al. | 260/463 |
| 3,114,762 | 12/1963 | Mador et al. | 260/463 |
| 3,227,741 | 1/1966 | Fenton | 260/463 |
| 3,444,133 | 5/1969 | Behr et al. | 260/47 ET |
| 3,625,995 | 12/1971 | Brattesani | 260/463 |
| 4,096,168 | 6/1978 | Hallgren | 260/463 |
| 4,096,169 | 6/1978 | Chalk | 260/463 |

Primary Examiner—Donald G. Daus
Assistant Examiner—M. C. Eakin
Attorney, Agent, or Firm—F. Wesley Turner; James C. Davis, Jr.; Leo I. MaLossi

[57] ABSTRACT

An improved catalytic aromatic carbonate process which comprises contacting under substantially anhydrous reaction conditions a phenol, carbon monoxide, an oxidant, a base, and the Group VIIIB element selected from ruthenium, rhodium, palladium, osmium, iridium or platinum. The resulting aromatic mono- and poly-carbonates are useful in the preparation of polycarbonates or as polycarbonates per se, respectively, which can be molded or formed into films, sheets, fibers, laminates or reinforced plastics by conventional techniques.

56 Claims, No Drawings

CATALYTIC AROMATIC CARBONATE PROCESS

This application is a continuation in part of application Ser. No. 731,494, filed Oct. 12, 1976, abandoned.

CROSS-REFERENCE TO RELATED APPLICATIONS

This invention is related to U.S. patent application Ser. No. 834,534, filed Sept. 19, 1977—a continuation of Ser. No. 731,443 filed Oct. 12, 1976, now abandoned; and U.S. Pat. No. 4,096,168 issued June 20, 1978 filed Oct. 12, 1976; and A. J. Chalk's U.S. patent application Ser. No. 892,497, filed Apr. 3, 1978 a continuation-in-part of Ser. No. 731,495, filed Oct. 12, 1976, now abandoned, and U.S. Pat. No. 4,096,169, issued June 20, 1978, also filed Oct. 12, 1976. All of the aforesaid applications are assigned to the same assignee as the assignee of this application.

BACKGROUND OF THE INVENTION

1. Field of the Invention

This invention relates to an improved catalytic aromatic carbonate process which comprises contacting under substantially anhydrous reaction conditions a phenol, carbon monoxide, an oxidant, a base, a Group VIIIB element selected from ruthenium, rhodium, palladium, osmium, iridium or platinum.

2. Description of the Prior Art

A. J. Chalk recognized—as broadly disclosed in the Chalk patent application referenced hereinbefore (Ser. No. 731,495, now abandoned)—that aromatic carbonates can be prepared by contacting a phenol, carbon monoxide, an oxidant, a base and the Group VIIIB element selected from ruthenium, rhodium, palladium, osmium, iridium or platinum.

Unexpectedly, I have found that optimum aromatic carbonate process yields result when a phenol, carbon monoxide, an oxidant, a base, and the Group VIIIB element are contacted under substantially anhydrous reaction conditions. Further, unexpectedly, I have found that more optimum aromatic carbonate process yields result when my process is carried out in the presence of a phase transfer agent, a manganese redox cocatalyst, and an alkali metal or alkali earth metal base.

DESCRIPTION OF THE INVENTION

This invention embodies an improved catalytic aromatic carbonate process which comprises contacting under substantially anhydrous reaction conditions a phenol, carbon monoxide, a Group VIIIB element selected from ruthenium, rhodium, palladium, osmium, iridium or platinum.

The reactants and the resulting reaction products of my process can be illustrated by the following general equations which are furnished for illustrative purposes only since the reaction mechanisms involved in the preparation of aromatic monocarbonates (Eq. 1) and polycarbonates (Eq. 2) may be much more complex:

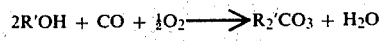
Eq. 1

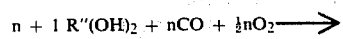
Eq. 2

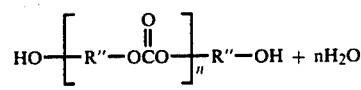

wherein R is an alkyl radical (including cycloalkyl), R' is an aryl radical, R" is an arene radical, and n is a number at least equal to 1.

Any of the phenols, solvents, bases, ligands, the Group VIIIB elements, oxidants—including redox cocatalysts, or reaction parameters relative to time, temperature and pressure disclosed in A. J. Chalk's copending Ser. No. 731,495, now abandoned, referenced herein can be employed in my process. Also, any of the amounts disclosed in the aforementioned A. J. Chalk Ser. No. 731,495, now abandoned relative to the aforementioned phenols, solvents, etc. can also be employed in a like manner in my process. In general, the preferred reactants and reaction conditions disclosed in A. J. Chalk's copending application Ser. No. 731,495, now abandoned, are also preferred in my process. Accordingly, their descriptions are hereby incorporated herein in their entirety.

Any nuclearly hydroxy substituted aromatic compound can be used in my process and is defined herein and in the appended claims as "a phenol". Illustratively the phenol (or phenolic reactants) can be described by the formula:

wherein $R_a$ represents an aromatic radical, where the —OH radical is attached directly to an aromatic ring carbon atom and x is a number being at least equal to 1, advantageously from 1 to 4, and preferably from 1 to 2. The $R_a$ radical can be carbo- or hetero-monocyclic, polycyclic, or fused polycyclic, and can have two or more cyclic systems (monocyclic, polycyclic or fused polycyclic systems) which are connected to each other or by bi- or multivalent radicals.

Preferred phenolic reactants are phenols containing from 6 to 30, and more preferably from 6 to 15 carbon atoms. Illustrative of commercially important phenolic reactants included within the above description are the following: phenol itself (hydroxy benzene), napthol, ortho-, meta-, or paracresol, catechol, cumenol, xylenol, resorcinol, the various isomers of dihydroxydiphenyl, the isomers of dihydroxynapthalene, bis(4-hydroxyphenyl)propane-2,2,α,α'-bis(4-hydroxyphenyl)-p-diisopropylbenzene, 4,4'-dihydroxy-3,5,3',5'-tetrachlorophenyl-propane-2,2,4,4'-dihydroxy-3,5,3',5'-tetrachloro-phenylpropane-2,2 and 4,4'-dihydroxy-3,5,3',5'-tetrachloro-phenylpropane-2,2 and 4,4'-dihydroxy-3,5,3',5'-tetrabromo-phenylpropane 2,2,phloroglucinol, dihydroxy oligomers, for example an oligomer derived from bisphenol-A, etc.

A generally preferred bisphenol that can be used in my process can be described by the following formula:

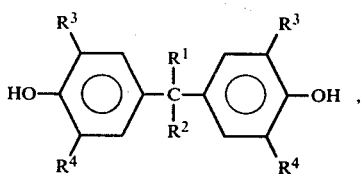
II.

where $R^1$ and $R^2$ are hydrogen, $C_{1-4}$ alkyl or phenyl, at least one of $R^3$ is hydrogen and the other is hydrogen or $C_{1-4}$ alkyl, and at least one of $R^4$ is hydrogen and the other is hydrogen or $C_{1-4}$ alkyl. Especially preferred is bis(4-hydroxyphenyl) propane-2,2, also commonly known as "bisphenol-A" (BPA).

Any Group VIIIB element, defined herein and in the appended claims as "the Group VIIIB element", can be employed subject to the proviso that it is selected from ruthenium, rhodium, palladium, osmium, iridium or platinum. The Group VIIIB elements can be employed in any of their well-known oxidation states as well as their zero valent elemental, i.e. metallic, form.

Illustratively, the Group VIIIB elements can be present in ionic, inorganic or organic compound or complex, etc. forms. The Group VIIIB elements can be employed in oxide, halide, nitrate, sulfate, oxalate, acetate, carbonate, propionate, hydroxide, tartrate, etc., forms.

The Group VIIIB elements can be employed in complex form, e.g. with ligands, such as carbon monoxide, nitriles, tertiary amines, phosphines, arsines, or stibines, etc., and illustratively are often represented by those skilled in the art as mono-, di-, or poly-nuclear Group VIIIB element forms. Generally, the dimeric or polymeric forms are considered to contain Group VIIIB atoms bridged by ligands, halogens, etc. Preferably the Group VIIIB elements form homogeneous mixtures when combined with the phenolic reactants, especially when the process is carried out under liquid phase reaction conditions.

Illustrative of the generally preferred Group VIIIB element compounds or complexes that can be used in my process follow: Ru, $RuCl_2$, $RuBr_2$, $RuI_2$, $Ru(CO)_2Cl_2$, $Ru(CO_2I_2)$, $Ru(CO)_4$—$Cl_2$, $Ru(CO)_4Br_2$, $Ru(CO)_4I_2$, $RuCl_3$, $RuBr_3$, $RuI_3$, etc., Pd, $PdCl_2$, $PdBr_2$, $PdI_2$, $[Pd(CO)Cl_2]_2$, $[Pd(CO)Br_2]_2$, $[Pd(CO)I_2]_2$, $(C_6H_5CN)_2PdCl_2$, $PdCl_4$, $Pd(OH)_2$—$(CNC_4H_9)_2$, $PdI_2(CNC_6H_5)_2$, $Pd(OH)_2(CNCH_3OC_6H_5)_2$, $Pd(CNC_4H_9)_4$, etc., Rh, $Rh(CO)Cl_2$, $Rh(CO)Br_2$, $Rh(CO)I_2$, $Rh_2Cl_2(CO)_2$, $Rh_2(CO)_4Cl_2$, $Rh_2(CO)_4Br_2$, $Rh_2(CO)_4I_2$, $[Rh(CO)_2Cl]_2$, $RhCl_3$, $RhBr_3$, $RhI_3$, etc., Os, $Os(CO)_3Cl_2$, $Os(CO)_3Br_2$, $Os(CO)_3I_2$, $Os(CO)_4Cl_2$, $Os(CO)_4Br_2$, $Os(CO)_4I_2$, $Os(CO)_8Cl_2$, $Os(CO)_8Br_2$, $Os(CO)_8I_2$, $OsCl_2$, $OsCl_3$, $OsI_2$, $OsI_3$, $OsBr_3$, $OsBr_4$ and $OsCl_4$, etc., Ir, $IrCl_3$, $IrCl_3(CO)$, $Ir_2(CO)_8$, $IrCl_3$, $IrBr_3$, $IrCl_3$, $IrBr_4$, $IrI_4$, etc., Pt, $PtCl_2$, $PtBr_2$, $PtI_2$, $Pt(CO)_2Cl_2$, $Pt(CO)_2Br_2$, $Pt(CO)_2I_2$, $Pt(CO)_2Cl_4$, $Pt(CO)_2Br_4$, $Pt(CO)_2I_4$, $Pt(CO)_3Cl_4$, $Pt(CO)_3Br_4$, $Pt(CO)_3I_4$, $PtCl_2(CNC_6H_5)_2$, etc.

Illustrative of ligands that can be associated with the Group VIIIB elements in complex form—other than and, optionally, in addition to carbon monoxide—include organic tertiary amines, phosphines, arsines and stibine ligands of the following formula:

$(E)_3Q$, wherein, independently, each E is selected from the radicals Z and OZ, where independently each Z is selected from organic radicals containing from 1 to 20 carbon atoms, and wherein independently each Q is selected from nitrogen, phosphorus, arsenic or antimony. Preferably, the organic radicals are free of active hydrogen atoms, reactive unsaturation, and are oxidatively stable. More preferably, the E groups are alkyl, cycloalkyl and aryl radicals and mixtures thereof, such as alkaryl, aralkyl, alkcycloalkyl containing from 1 to 10 carbon atoms, and even more preferably each E is an aryl group containing from 6 to 10 carbon atoms.

Illustrative of the generally known presently preferred Group VIIIB complexes which contain ligands include the following: $RuCl_2[P(C_6H_5)_3]_4$, $[Rh(CO)_2Cl]_2$, $trans[(C_2H_5)_5P]_2PdBr_2$, $[P(C_4H_9)_3]_2PdCl_4$, $[(C_6H_5)_3P]_3IrCl_3(CO)$, $[(C_6H_5)_3As]_3IrCl_3(CO)$, $[(C_6H_5)_3Sb]_3IrCl_3(CO)$, $[(C_6H_5)_3P]_2PtCl_2$, $[(C_6H_5)_3P]_2PtF_2$, $[(C_6H_5)_3P]_2PtF_2(CO)_2$, $Pt[(C_6H_5)_3P]_2(CO)_2$, etc.

The Group VIIIB element compounds and/or complexes can be prepared by any method well-known to those skilled in the art including the methods referenced in the following publications:

*Treatise on Inorganic Chemistry*, Volume II, H. Remy, Elsevier Publishing Co. (1956);

*Reactions of Transition-Metal Complexes*, J. P. Candlin, K. A. Taylor and D. T. Thompson, Elsevier Publishing Co. (1968) Library of Congress Catalog Card No. 67-19855;

*Organic Syntheses Via Metal Carbonyls*, Vol. 1, I. Wender and P. Pino, Interscience Publishers (1968) Library of Congress Catalog Card No. 67-13965;

*The Organic Chemistry of Palladium*, Vols. I and II, P. M. Maitlis, Academic Press (1971) Library of Congress Catalog Card No. 77-162937;

*The Chemistry of Platinum and Palladium*, F. R. Hartley, Halsted Press (1973);

The process can be carried out in the absence of any solvent, e.g. where the phenolic reactant acts as both a reactant and a solvent, however preferably is carried out in the presence of a solvent, and more preferably solvents of the general class: methylene chloride, ethylene dichloride, chloroform, carbon tetrachloride, tetrachloroethylene, nitromethane, hexane, 3-methylpentane, heptane, cyclohexane, methylcyclohexane, cyclohexane, isooctane, p-cymene, cumene, decalin, toluene, benzene, diphenylether, dioxane, thiophene, dimethyl sulfide, ethyl acetate, tetrahydrofuran, chlorobenzene, anisol, bromobenzene, o-dichlorobenzene, methyl formate, iodobenzene, acetone, acetophenone, etc., and mixtures thereof.

In general, the process can be carried out in any basic reaction medium, preferably, that provided by the presence of any inorganic or organic base or mixtures thereof. Representative of basic species which can be employed are the following: elemental alkali and alkaline earth metals; basic quaternary ammonium, quaternary phosphonium or tertiary sulfonium compounds; alkali or alkaline earth metal hydroxides; salts of strong bases and weak acids; primary, secondary or tertiary amines; etc. Specific examples of the aforementioned are sodium, potassium, magnesium metals, etc.; quaternary ammonium hydroxide, tetraethyl phosphonium hydroxide, etc.; sodium, potassium, lithium, and calcium hydroxide; quaternary phosphonium, tertiary sulfonium, sodium, lithium and barium carbonate, sodium acetate, sodium benzoate, sodium methylate, sodium thiosulfate, sodium sulfide, sodium tetrasulfide, sodium cyanide, sodium hydride, sodium borohydride, potassium fluoride, triethylamine, trimethylamine, allyldiethylamine, benzyldimethylamine, dioctylbenylamine, dimethylphenethylamine, 1-dimethylamino-2-phenylpropane, N,N,N',N'-tetramethylenediamine, 2,2,6,6-tetramethylpyridine, N-methyl piperidine, pyridine, 2,2,6,6-N-pentamethylpiperidine, etc. Especially preferred bases are sterically hindered amines, e.g. diisopropylmonoethylamine, 2,2,6,6,N-pentamethylpiperidine, etc.

Any oxidant can be employed in the herein claimed process subject to the proviso that the oxidant is a compound or complex of a periodic Group IIIA, IVA, VA, VIA, IB, IIB, VIB, VIIB or VIIIB, element and the oxidant has an oxidation potential greater than or more positive than the Group VIIIB element. Typical oxidants for the Group VIIIB elements are compounds of copper, iron, manganese, cobalt, mercury, lead, cerium, uranium, bismuth, chromium, etc. Of these, copper salts are preferred. The anion of the salt may be a $C_{1-20}$ carboxylate, halide, nitrate sulfate, etc., and preferably is a halide., e.g., chloride, bromide, iodide, or fluoride. Illustrative of typical oxidant compounds are cupric chloride, cupric bromide, cupric nitrate, cupric sulfate, cupric acetate, etc. In addition to the compounds described above, gaseous oxygen may be employed as the sole oxidant in the herein claimed process. Typically, compounds or complexes of a periodic Group IIIA, IVA, VA, IB, IIB, VB, VIB, VIIB, and VIIIB element are preferably employed, in conjunction with oxygen, as redox co-catalysts in order to enhance the rate of oxidation of the Group VIIIB metal by gaseous oxygen.

As used herein and in the appended claims, the expression "complexes" includes coordination or complex compounds well-known to those skilled in the art such as those described in *Mechanisms of Inorganic Reactions*, Fred Basolo and Ralph G. Pearson, 2nd Edition, John Wiley and Sons, Inc. (1968). These compounds are generally defined herein as containing a central ion or atom, i.e. a periodic Group IIA, IVA, VA, VIA, IB, IIB, VIB, VIIB or VIIIB element and a cluster of atoms or molecules surrounding the periodic group element. The complexes may be nonionic, or a cation or anion, depending on the charges carried by the central atom and the coordinated groups. The coordinated groups are defined herein as ligands, and the total number of attachments to the central atom is defined herein as the coordination number. Other common names for these complexes include complex ions (if electrically charged), Werner complexes, coordination complexes or, simply, complexes.

The redox components as a class comprise any compound or complex of a periodic Group IIIA, IVA, VA, IB, IIB, VB, VIB, VIIB and VIIIB, which catalyze the oxidation of the Group VIIIB elements, i.e. ruthenium, rhodium, palladium, osmium, iridium or platinum in the presence of oxygen, from a lower oxidation state to a higher oxidation state.

Any source of oxygen can be employed, i.e., air, gaseous oxygen, liquid oyxgen, etc. Preferably either air or gaseous oxygen are employed.

Any amount of oxygen can be employed. Preferably the process is carried out under positive oxygen pressure, i.e., where oxygen is present in stoichiometric amounts sufficient to form the desired aromatic mono- or polycarbonate. In general, oxygen pressures within the range of from about 0.1 to 500 atmospheres, or even higher, can be employed with good results. Presently preferred are oxygen pressures within the range of from about ½ to 200 atmospheres.

Any amount of the oxidant can be employed. For example oxidant to phenol mole proportions within the range of from about 0.001:1 or lower to about 1000:1 or higher are effective; however preferably ratios from 0.1:1 to 10:1 are employed to insure an optimum conversion of phenol to aromatic carbonate. It is essential wherein an oxidant is employed—in the substantial absence of oxygen, i.e. not as a redox co-catalyst component—that the oxidant be present in amounts stoichiometric to carbonate moieties; i.e.,

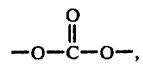

formed in the preparation of the aromatic carbonates.

Any amount of redox co-catalyst conponent can be employed. For example, redox catalyst to phenol mole proportions within the range of from about 0.0001:1 to lower to about 1000:1 or higher are effective; however, preferably ratios of from 0.0001:1 to 1:1, and more preferably 0.001:1 to 0.01:1 are employed.

Any amount of base can be employed. In general, effective mole ratios of base to the Group VIIIB elements are within the range of from about 0.00001:1 to about 100:1 or higher, preferably from 0.5:1 to about 10:1, and more preferably from 1:1 to 2:1. Generally, mole ratios of at least 1:1 enhance both the reaction rate and the yield of aromatic carbonate.

Any amount of the Group VIIIB element can be employed. For example, Group VIIIB element to phenol mole proportions within the range of from about 0.0001:1 or lower to about 1000:1 or higher are effective; however, preferably ratios of from 0.001 to 0.01 are employed in my catalytic reaction.

Any amount of carbon monoxide can be employed. Preferably the process is carried out under positive carbon monoxide pressure; i.e., where carbon monoxide is present in stoichiometric amounts sufficient to form the desired aromatic mono- or polycarbonate. In general, carbon monoxide pressures within the range of from about ½ to 500 atmospheres, or even higher, can be employed with good results. Presently preferred are CO pressures within the range of from 1 to 200 atmospheres.

Any amount of solvent, preferably inert, can be employed. In general, optimum solvent to phenolic reactant mole proportions are from 0.5:99.5 to 99.5:0.5, preferably from 50:50 to 99:1.

Any reaction temperature can be employed. In general, optimum reaction temperatures are 0° C., or even lower, to 200° C., or even higher and more often 0° C. to 50° C.

Any reaction time period can be employed. Generally optimum reaction time periods are about 0.1 hour or even less to about 10 hours or even more.

Following some of the procedures described herein, aromatic salicylates can be formed. These aromatic salicylates, i.e. aromatic compounds which can be defined as "salicylate", can be generically described by the following formula:

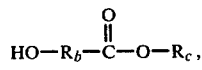

wherein R$_b$ represents an aromatic radical wherein the hydroxyl radical is positioned ortho relative to the carboxylate, i.e.

radical, and R$_c$ represents an aromatic radical. The R$_b$ and R$_c$ radicals can be carbo- or hetero-monocyclic, polycyclic, or fused polycyclic, and can have two or more cyclic systems (monocyclic, polycyclic or fused polycyclic systems) which are directly joined to each other by single or double valence bonds, or by bi- or multivalent radicals.

The separation and recovery of the salicylates is described in the U.S. patent application Ser. No. 731,443, now abandoned of J. E. Hallgren, filed Oct. 10, 1976.

The reaction parameters essential to the practice of my process comprise any of Chalk's process parameters, however also includes carrying out my process under substantially anhydrous reaction conditions, e.g. where any water formed during the course of the reactions involved in my process is removed from the reaction environment by any means, such as the use of azeotropic distillation techniques, a drying agent, etc. In a preferred embodiment my process is carried out under reaction conditions wherein no measurable amount of water can be detected within the reaction medium during the course of the reaction. Substantially anhydrous reaction conditions are defined herein and in the appended claims as the practice of my process employing any separation techniques which will remove any measurable amount of water, formed as described hereinbefore by Equations 1 and 2, from the reaction medium—including the use of any drying agent. Where drying agents are employed, they are preferably inert and are any of those known to those of ordinary skill in the art. The agents can be classified by any means, e.g. regenerative or nonregenerative; liquid or solid; chemical reaction, i.e. the formation of a new compound or a hydrate; physical absorption at constant or variable relative humidity; adsorption, etc. Preferably, the drying agent(s) employed in my process have high capacity and/or efficiency and preferably both in removing moisture from the reaction medium. As employed herein, the term "capacity" refers to the amount of water that can be removed from a given weight of the reaction medium and the efficiency refers to the degree of dryness that can be produced by the drying agent. Among the many drying agents that can be employed are activated alumina, barium oxide, calcium chloride, calcium oxide, calcium sulfate, lithium chloride, molecular sieves, e.g. drying agents made from natural or synthetic crystalline alkali metal aluminosilicates of the zeolite type, etc. Preferred drying agents used in the practice of my invention are natural and synthetic zeolites well known to the art such as those described in detail in the publication *Molecular Sieves*, Charles K. Hersh, Reinhold Publishing Company, New York (1961), which is incorporated herein in its entirety by reference. Representative natural zeolites which may be used include those in Table 3-1, page 21 of the Hersh reference. Additional useful zeolite drying agents are set forth in *Organic Catalysis Over Crystalline Aluminosilicates*, P. B. Venuto and P. S. Landis, Advances in Catalysis, Vol. 18, pp. 259-371 (1968), which is also incorporated herein in its entirety by reference. Particularly useful molecular sieves are those designated by the Linde Division of the Union Carbide Corporation as zeolite types A, X and Y, described in U.S. Pat. Nos. 2,882,243, 3,130,007 and 3,529,033, which descriptions are also incorporated herein in their entirety by reference. Other zeolites are, of course, included within the scope of this invention.

In another embodiment of my process, preferably a manganese or cobalt redox co-catalyst is employed.

Illustrative of manganese redox co-catalysts commonly referred to as manganese chelates are those represented by the general formula LMn—wherein L is a ligand derived from an omega-($\omega$)-hydroxyoxime or an ortho-(o)-hydroxyareneoxime, including mixtures thereof, and Mn is the transition metal manganese. Illustratively, the manganese can be employed in any of its oxidation states, e.g. from $-1$ to $+7$. An $\omega$-hydroxyoxime ligand, represented as "L" in the general formula LMn, can be described by the following formula:

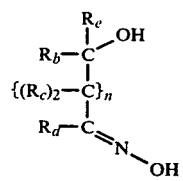  I.

wherein independently each R$_b$, R$_c$, R$_d$ and R$_e$ is selected from the group consisting of hydrogen, acyclic and cyclic hydrocarbon radicals, and n is a positive integer equal to 0 or 1.

An ortho-hydroxyareneoxime ligand, represented as "L" in the general formula LMn, can be described by the following formula:

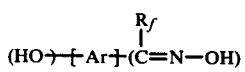  II.

wherein R$_f$ is independently selected from the group consisting of hydrogen and acyclic hydrocarbon radicals, Ar is at least a divalent arene radical having at least one —OH radical and at least one

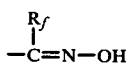

radical attached directly to an ortho position arene ring carbon atom. Methods for the preparation of manganese chelate complexes including mixtures thereof are described in U.S. Pat. Nos. 3,956,242, 3,965,069 and 3,972,851, etc. The description of the manganese complexes as set out therein are incorporated herein in their entirety by reference.

Illustrative of well-known manganese redox co-catalysts are described by the following formulae:

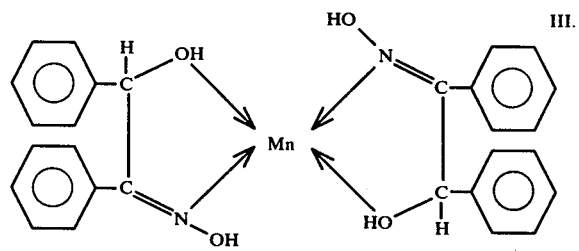  III.

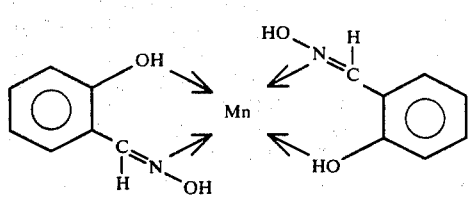

Illustrative of other manganese ligands that can be associated with LMn complexes—which presently belong to an even more generally preferred "L" class—are alpha(α)-diketone or a beta-(β)-diketone ligands, including mixtures thereof. In general, α-diketone ligands can be described by the following formula:

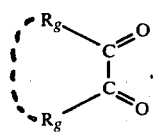

wherein independently each $R_g$ is selected from the group consisting of hydrogen, acyclic and cyclic hydrocarbon radicals, primary amines (—NH$_2$), secondary amines (—NHR$_h$), tertiary amines (—NR$_h$R$_i$), hydroxyl radicals (—OH), oxyhydrocarbon radicals (—OR$_j$), and the halogens (F, Cl, Br or I), R$_h$, R$_i$, R$_j$ being the same as either R$_g$ as defined above, subject to the proviso that each R$_g$ may be the same, different or conjoint.

In general, β-diketone ligands can be described by the following formula:

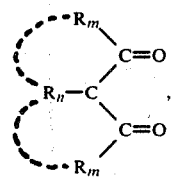

wherein independently each R$_m$ and R$_n$ are the same, different or conjoint, and are selected from the same R$_g$ groups described in Formula V above.

Illustrative of an α-diketone is tropolone commonly described by the formulae:

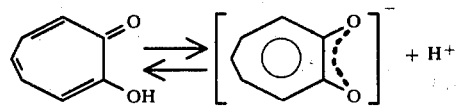

and a β-diketone is acetylacetone, commonly described by the formulae:

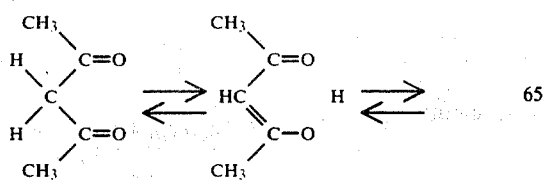

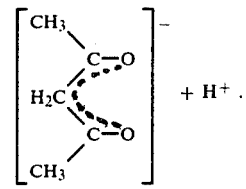

Other well-known diketones include
2-acetyl-1,3-cyclohexanedione,
2-acetyl-1-tetralone,
benzofuran-2-yl methyl ketone,
1-benzoylacetone,
3-benzylidene-2,4-pentanedione,
biacetyl,
benzil,
dibenzoylmethane,
2,2-dimethyl-6,6,7,7,8,8,8-heptafluoro-3,5-octanedione,
2,4-pentanedione,
2,4-pentanedione, thallium(I) salt,
2,2,6,6-tetramethyl-3,5-heptanedione,
thenoyltrifluoroacetone,
triacetylmethane, etc.

The α and β-diketones can be prepared by any method well-known to those skilled in the art including those described and referenced in *Advanced Inorganic Chemistry*, F. A. Cotton and G. Wilkinson, Interscience Publishers, cc. 1972, John Wiley & Sons, Inc.

Illustrative of well-known cobalt redox co-catalysts are those commonly referred to as cobalt chelates and includes those represented by the general formula:

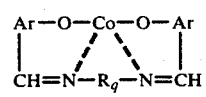

wherein Ar represents a divalent arene radical and R$_q$ represents a divalent organic radical containing at least 2 carbon atoms. Methods for the preparation of cobalt chelate complexes including mixtures thereof are described in U.S. Pat. Nos. 3,455,880, 3,444,133 and 3,781,382, etc. The description of the cobalt complexes as set out therein are incorporated herein in their entirety by reference.

Generally presently preferred cobalt chelate complexes are described by the following formulas:

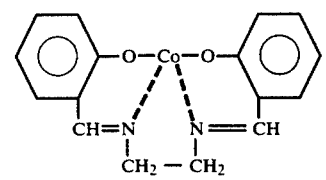

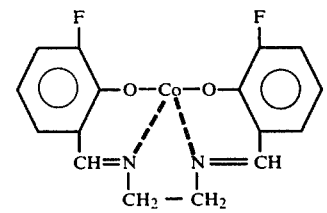

-continued

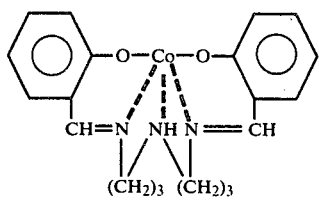

X.

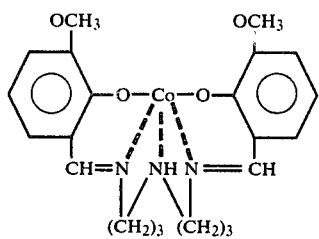

XI.

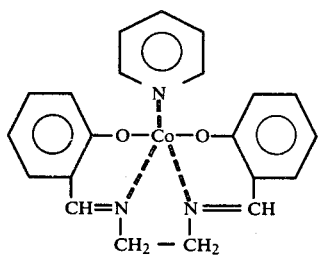

XII.

Since manganese and cobalt complexes can coordinate with water, oxygen, alcohol, amines, etc., such coordination compounds are included within the context as oxidants in the practice of my invention.

In another preferred embodiment, my process is carried out in the presence of an organic phase transfer agent (PTA). Generally effective phase transfer agents include quaternary ammonium compounds, quaternary phosphonium compounds, tertiary sulfonium compounds, crown ether compounds, chelated cationic salts, cryptates, i.e. any agent which is soluble in the organic phase and which enhances the transfer, maintenance or retention of a halide, and in a preferred embodiment a bromide, in the organic phase in the reaction environment.

Illustrative of well-known onium phase transfer agents are those described by C. M. Starks in J.A.C.S. 93, 195 (1971), e.g. ammonium, phosphonium and sulfonium compounds represented by the following formulas, respectively:

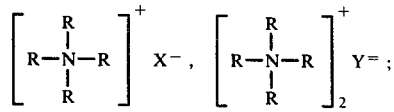

XIII.

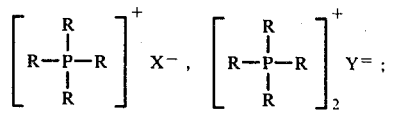

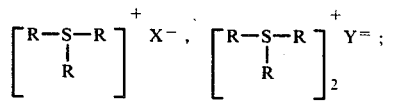

wherein each R is independently selected from acyclic and cyclic hydrocarbon radicals, e.g. alkyl, alkenyl, cycloalkyl, cycloalkenyl, aryl, including mixtures and combinations thereof, preferably each R having from about 1 to about 30 carbon atoms, and more preferably from about 2 to about 15 carbon atoms, each $X^-$ is selected from the group consisting of $Cl^-$, $Br^-$, $F^-$, $I^-$, $CH_3SO_3-$, $CH_3CO_2-$, $CF_3CO_2-$ or $OH-$, and each $Y^=$ is selected from the group consisting of $SO_4^=$, $CO_3^=$, or $C_2O_4^=$. Illustrative examples of presently preferred phase transfer agents follow:

tetramethylammonium chloride,
    tetraethylphosphonium iodide,
    tripropylsulfonium bromide,
    triallylsulfonium acetate,
    tetrabutylammonium fluoride,
    tetracyclohexylphosphonium hydroxide,
    triphenylammonium bromide,
    tricaprylmonomethylammonium chloride,
    tetradodecylphosphonium trifluoroacetate,
    trioctadecylsulfonium sulfate,
    tetraeicosylammonium carbonate,
    tetratricosylphosphonium oxalate,
    tritriacontylsulfonium methane sulfonate, etc.

The onium compounds can be prepared by any method well-known in the art including e.g. the preparation of onium halides by the familiar addition reactions of tertiary amines, tertiary phosphines and sulfides with alkyl halides.

Illustrative of well-known crown ether phase transfer agents are any of those described in Aldrichimica ACTA 9, Issue #1 (1976) Crown Ether Chemistry:Principles and Applications, G. W. Gokel and H. D. Durst, as well as C. J. Pederson in U.S. Pat. No. 3,622,577. Illustrative of a presently preferred crown ether phase transfer agent is 18-crown-6 represented by the formula:

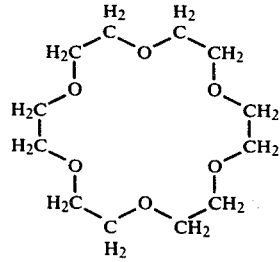

XIV.

Although 18-crown-6 is limited to oxygen, carbon and hydrogen atoms associated with the ring structure—in other crown ether atoms—sulfur, nitrogen, phosphorus, etc.,—can be substituted for oxygen within the ring structure. Other well-known crown ethers include 12-crown-4, 15-crown-5, dibenzo-18-crown-6, dicyclohexyl-18-crown-6, among many others. The crown ether descriptions referred to in the aforementioned publications are incorporated herein in their entirety by reference. The crown ethers can be prepared by methods well-known in the art including among others the reactions described in Pederson's U.S. Pat. No. 3,622,577.

Illustrative of well-known chelated cationic salts are alkali or alkaline earth metal diamine halides. Specific examples follow:

lithium(tetramethylethylenediamine)$_2$bromide,
    sodium(tetraisopropylethylenediamine)$_2$chloride,
    potassium(tetrabutylethylenediamine)$_2$fluoride, calcium(tetramethylpropylenediamine)₃iodide,
magnesium(tetraethylpropylenediamine)₂bromide,
etc.

In my process, any amount of drying agent can be employed. Those skilled in the art can determine, by means of routine experimentation, the optimum amounts of any particular drying agent which is selected and used in the practice of my invention. For example, those skilled in the art can readily estimate the optimum amounts of molecular sieve required for selective absorption of water by routine reference to Linde ® Company, molecular Types 3A and 4A "Water Data Sheets" published and distributed by Union Carbide Corporation.

In a still more preferred embodiment my invention is carried out in a reaction environment which contains at least one of each of the following groups (A), (B) and (C):

(A) a base comprising any elemental alkali or alkaline earth metal base including organic or inorganic basic compounds thereof, e.g. lithium, sodium, potassium, calcium, or barium hydroxide; sodium, lithium or barium carbonate, sodium acetate, sodium benzoate, sodium methylate, etc., including mixtures thereof. Presently preferred are a strong alkali metal hydroxide bases, e.g. sodium hydroxide, and potassium hydroxide, because of their efficacy and economics in this embodiment.

(B) A phase transfer agent comprising any phase transfer agent. Presently preferred are onium halides where at least one of and more preferably each of the R groups of formula XIII contain at least 4 carbon atoms, and each anion X⁻ is selected from a halide, especially preferred being chloride or bromide, and more especially preferred being bromide. Illustrative examples include tetrabutylammonium bromide, tetrabutylphosphonium bromide, etc.

(C) A manganese redox co-catalyst of any α-diketone or β-diketone, or mixtures thereof—preferably because of their efficacy—manganese complexes associated with acetylacetone, e.g. manganese(II)-bis(acetoacetonate).

In another preferred embodiment enhanced reaction rates are generally obtained wherein at least one of the groups defined in paragraphs (A), (B) and (C) set out above are employed, subject to the proviso that the phase transfer agent contains a halide counterion—especially where the counterion is a bromide ion—and further subject to the proviso that the phase transfer agent having a halide associated therewith is present in an amount in excess of the molar amounts of the base.

Any amount of phase transfer agent can be employed. In addition, effective mole ratios of phase transfer agents to "the Group VIIIB element" are within the range of from about 0.00001:1 to about 1000:1 or higher, preferably from about 0.05:1 to about 100:1 and more preferably from about 10:1 to 20:1.

In order that those skilled in the art may better understand my invention, the following examples are given which are illustrative of the best mode of this invention, however, these examples are not intended to limit the invention in any manner whatsoever. In the examples, unless otherwise specified, all parts are by weight and the reaction products were verified by infrared spectrum, C-13 nuclear magnetic resonance and mass spectrometry.

EXAMPLE I

A procedure, which is not an example of this invention, for the preparation of 4,4'-(α,α-dimethylbenzyl)-diphenylcarbonate under carbon monoxide and oxygen pressure and in the absence of a drying agent.

A reaction medium containing p-cumylphenol, bis(-benzonitrile)palladium(II) dichloride, diisopropyl-monoethylamine and copper dibromide was formulated. The mole proportions of the ingredients were as follows 100:2:15:8, respectively. The reaction medium was charged with sufficient carbon monoxide to raise the pressure to 31 psi and sufficient oxygen to raise the pressure from 31 psi to 62 psi. Subsequent workup and analysis of the reaction identified a product yield of 8% of 4,4'-α,α(dimethylbenzyl)diphenylcarbonate of the formula:

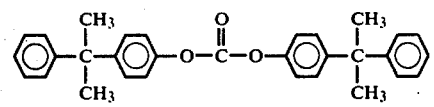

The number of carbonate moieties, i.e.

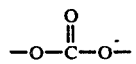

formed per mole of palladium metal was 4. Hereafter this number is referred to as the Group VIIIB "turnover value" of the reaction.

EXAMPLE II

Preparation of 4,4'(α,α-dimethylbenzyl)diphenylcarbonate under carbon monoxide and oxygen pressure and in the presence of a molecular sieve Type 4A—a commercial product of Union Carbide Corporation of the general chemical formula $0.96\pm0.04$ Na₂O.1.00 Al₂O₃.1.92±0.09 SiO₂.×H₂O.

The reaction medium contained p-cumylphenol, bis(-benzonitrile)palladium(II) dichloride, diisopropyl-monoethylamine, and copper dibromide which were present in the following mole proportions 100:2:16:8, respectively. The reaction medium was charged with carbon monoxide to 31 psi and oxygen to 62 psi as in Example I. Subsequent analysis identified a product yield of 31% of 4,4'-α,α(dimethylbenzyl)diphenylcarbonate. As illustrated by this example, the inclusion of a drying agent, e.g. a molecular sieve, significantly increases the yield of aromatic carbonate, e.g. by 400% when the yield of this example is compared with the yield of the procedure described in Example I.

EXAMPLE III

Preparation of 4,4'-(α,α-dimethylbenzyl)diphenylcarbonate using p-cumylphenol, carbon monoxide, 2,2,6,6,N-pentamethylpiperidine, palladium(II) dibromide, bis(benzoinoxime)manganese(II) and a molecular sieve.

A reaction vessel was charged with 2.12 g. (0.010 mole) of p-cumylphenol, 0.030 g. (0.00010 moles) of palladium(II) dibromide, 0.051 g. (0.00010 mole) of bis(benzoinoxime) manganese(II), 0.155 g. (0.0010 mole) of 2,2,6,6,N-pentamethylpiperidine, 30 ml. of methyl chloride and 2.0 g. of a Lindy Union Carbide 3A molecular sieve which had been activated by heating at 200° C. in vacuo. The Type 3A molecular sieve employed is a commercial product of Union Carbide Corporation produced from Type 4A molecular sieves through ionic exchange of about 75% of the sodium ions by potassium. Carbon monoxide and air were bubbled slowly through the reaction vessel mixture at room temperature for 18 hours. Gas chromatography indicated the presence of 0.495 g. (22.2% yield) of 4,4'-($\alpha,\alpha$-dimethylbenzyl)diphenylcarbonate. After 44 hours, reaction product contained 1.23 g. (55% yield) of the aromatic carbonate.

EXAMPLE IV

Preparation of 4,4'-($\alpha,\alpha$-dimethylbenzyl)diphenylcarbonate using p-cumylphenol, carbon monoxide, 2,2,6,6,N-pentamethylpiperidine, palladium(II) dibromide, manganese(II) bis(acetylacetonate) and a molecular sieve.

A reaction vessel was charged with 2.12 g. (0.010 mole) of p-cumylphenol, 0.026 g. (0.00010 moles) of palladium(II) dibromide, 0.075 g. (0.0030 moles) of manganese(II) acetylacetonate, 0.23 g. (0.0015 moles) of 2,2,6,6,N-pentamethylpiperidine, 30 ml. of methylene chloride and 2.0 g. of a 200° C. vacuo activated Linde Union Carbide 3A molecular sieve. Carbon monoxide and air were bubbled slowly through the reaction vessel mixture at room temperature for 16 hours. Liquid chromatography indicated the presence of 1.10 g. (49% yield) of 4,4'-($\alpha,\alpha$-dimethylbenzyl)diphenylcarbonate. After 55 hours, reaction product contained 1.69 g. (75% yield) of the aromatic carbonate.

EXAMPLE V

Preparation of 4,4'-($\alpha,\alpha$-dimethylbenzyl)diphenylcarbonate using p-cumylphenol, carbon monoxide, aqueous sodium hydroxide, palladium(II) dibromide, manganese(II) bis(acetylacetonate), a Type 3A molecular sieve, and a phase transfer agent, e.g. tetrabutylammonium bromide.

A reaction vessel was charged with 2.12 g. (0.010 mole) of p-cumylphenol, 0.026 g. (0.00010 moles) of palladium(II) dibromide, 0.075 g. (0.00030 moles) of manganese(II) bis(acetylacetonate), 0.515 g. (0.0016 moles) of tetrabutylammonium bromide, 0.176 g. (0.0013 moles) of a 25% aqueous sodium hydroxide solution, 30 ml. of methylene chloride, and 4.0 g. of a 200° C. vacuo activated Linde Union Carbide Type 3A molecular sieve. Carbon monoxide and air were bubbled slowly through the reaction vessel mixture at room temperature for 18 hours. Liquid chromatography indicated the presence of 1.35 g. (60% yield) of 4,4'-($\alpha,\alpha$-dimethylbenzyl)diphenylcarbonate. After 42 hours, reaction product contained 2.01 g. (89% yield) of the aromatic carbonate.

EXAMPLE VI

Preparation of 4,4'-($\alpha,\alpha$-dimethylbenzyl)diphenylcarbonate using p-cumylphenol, carbon monoxide, aqueous sodium hydroxide, palladium(II) dibromide, manganese(II) bis(acetylacetonate), a Type 3A molecular sieve, and a phase transfer agent, e.g. tetrabutylphosphonium bromide.

A reaction vessel was charged with 2.12 g. (0.010 mole) of p-cumylphenol, 0.026 g. (0.00010 moles) of palladium(II) dibromide, 0.075 g. (0.00030 moles) of manganese(II) bis(acetylacetonate), 0.542 g. (0.0016 moles) of tetrabutylphosphonium bromide, 0.216 g. (0.0013 moles) of a 25% aqueous solution of sodium hydroxide, 30 ml. of methylene chloride, and 4.0 g. of a 200° C. vacuo activated Linde Union Carbide Type 3A molecular sieve. Carbon monoxide and air were bubbled slowly through the reaction vessel mixture at room temperature for 16 hours. Liquid chromatography indicated the presence of 1.22 g. (54% yield) of 4,4'-($\alpha,\alpha$-dimethylbenzyl)diphenylcarbonate.

EXAMPLE VII

Preparation of 4,4'-($\alpha,\alpha$-dimethylbenzyl)diphenylcarbonate using p-cumylphenol, carbon monoxide, aqueous sodium hydroxide, palladium(II) dibromide, 3-fluoro-cobalt-salen, a Type 3A molecular sieve and a phase transfer agent, e.g. tetrabutylammonium bromide.

A reaction vessel was charged with 2.12 g. (0.010 mole) of p-cumylphenol, 0.026 g. (0.00010 moles) of palladium(II) dibromide, 0.109 g. (0.00030 moles) of 3-fluoro-cobalt-salen, 0.515 g. (0.0016 moles) of tetrabutylammonium bromide, 0.216 g. (0.0013 moles) of a 25% aqueous sodium hydroxide solution, 30 ml. of methylene chloride, and 4.0 g. of a 200° C. vacuo activated Linde Union Carbide Type 3A molecular sieve. Carbon monoxide and air were bubbled slowly through the reaction vessel mixture at room temperature for 16 hours. Liquid chromatography indicated the presence of 0.247 g. (11% yield) of 4,4'-($\alpha,\alpha$-dimethylbenzyl)-diphenylcarbonate.

EXAMPLE VIII

Preparation of 4,4'-($\alpha,\alpha$-dimethylbenzyl)diphenylcarbonate using p-cumylphenol, carbon monoxide, aqueous potassium hydroxide, palladium(II) dibromide, manganese(II) bis(acetylacetonate), a Type 3A molecular sieve, and a phase transfer agent, e.g. 18-crown-6.

A reaction vessel was charged with 2.12 g. (0.010 mole) of p-cumylphenol, 0.026 g. (0.00010 moles) of palladium(II) dibromide, 0.075 g. (0.00030 moles) of manganese(II) acetylacetonate, 0.34 g. (0.0013 moles) of 18-crown-6, 0.35 g. (0.0013 moles) of a 25% aqueous solution of potassium hydroxide, 30 ml. of methylene chloride, and 4.0 g. of a 200° C. vacuo activated Linde Union Carbide Type 3A molecular sieve. Carbon monoxide and air were bubble slowly through the reaction vessel mixture at room temperature for 16 hours. Liquid chromatography indicated the presence of 0.70 g. (31% yield) of 4,4'-($\alpha,\alpha$-dimethylbenzyl)diphenylcarbonate. After 64 hours, reaction product contained 1.58 g. (70% yield) of the aromatic carbonate.

EXAMPLES IX–XVII

Following the General Procedure of Example III, set out hereinbefore, a series of reactions were run employing various oxidants for the preparation of aromatic carbonates in the presence of molecular sieves. Summarized in Table I hereafter are the reaction parameters and products, i.e. the mole proportions of Group VIIIB element: redox component: phenolic reactant: base, the percent conversion of the phenolic reactant to aromatic carbonate, the reaction time and the turnover value.

In all of the examples, the phenolic reactant was p-cumylphenol and the base was 2,2,6,6,N-pentamethylpiperidine except for Example XV where the base was triethylamine. The Group VIIIB element in Examples III, X, XI, and XV was palladium(II) dibromide, and in Examples XII, XIII and XIV was palladium(I) monocarbonyl monobromide. The redox co-catalyst employed in addition to the oxidant oxygen in each example is tabulated in Table I. Example XVI was a control run analogous to Example IX except that the Group VIIIB element was excluded from the reaction and the reaction time was extended.

oxidation state, and can be re-employed, that is recycled, in the aromatic process described herein.

TABLE I

| Example No. | Redox Component | Group VIIIB | Redox Component | Phenolic Reactant | Base | Percent (%) Conversion | Reaction Time (hr) | Turn Over Value |
|---|---|---|---|---|---|---|---|---|
| IX | Mn(II)(benzoinoxime)$_2$ | 1 | 3 | 100 | 20 | 96 | 44 | 95 |
| X | Mn(II)(benzoinoxime)$_2$ | 1 | 1 | 100 | 10 | 55 | 44 | 54 |
| XI | (C$_4$H$_9$N)$_2$Mn(II)Br$_4$ | 1 | 3.5 | 100 | 35 | 20 | overnight | 19 |
| XII | Mn(II)Br$_2$ . 4H$_2$O | 1 | 10 | 100 | 100 | 20 | 165 | 19 |
| XIII | Cu(I)Br | 1 | 10 | 100 | 20 | 21 | 110 | 20 |
| XIV | Co(salen)pyridine | 1 | 3 | 100 | 15 | 90 | 192 | 89 |
| XV | Co(salen)pyridine | 1 | 3 | 100 | 15 | 8 | 20 | 7 |
| XVI | VBr$_3$ | 1 | 3 | 100 | 15 | 1.7 | 72 | 0.7 |
| XVII | Mn(II)(benzoinoxime)$_2$ | 0 | 3 | 100 | 20 | non-detectable | 168 | 0 |

EXAMPLE XVIII

Preparation of a polycarbonate of bisphenol-A by contacting bis(4-hydroxyphenyl)propane-2,2, carbon monoxide, aqueous sodium hydroxide, palladium(II) dibromide, manganese(II) bis(acetylacetonate), a Type 3A molecular sieve, and a phase transfer agent, e.g. tetrabutylammonium bromide.

A reaction vessel was charged with 3.42 g. (0.015 mole) of bisphenol-A, 0.08 g. (0.00030 moles) of palladium(II) dibromide, 0.225 g. (0.00090 moles) of manganese(II) acetylacetonate, 1.93 g. (0.0060 moles) of tetrabutylammonium bromide, 0.38 g. (0.0048 moles) of a 50% aqueous solution of sodium hydroxide, 30 ml. of methylene chloride, and 4.0 g. of a 200° C. vacuo activated Linde Union Carbide Type 3A molecular sieve. Carbon monoxide and air were bubbled slowly through the reaction vessel mixture at room temperatue for 96 hours. Liquid chromatography indicated the presence of polycarbonate, $\overline{M}_n=609$, $\overline{M}_w=824$.

EXAMPLE XIX

Preparation of a polycarbonate of bisphenol-A by contacting bis(4-hydroxyphenyl)propane-2,2, carbon monoxide, manganese(II)bis(benzoinoxime), 2,2,6,6,N-pentamethylpiperidine, palladium(II)dibromide, oxygen, a molecular sieve Type 3A and air.

A flask was charged with 4.56 g. (20.0 mmol.) of bis(4-hydroxyphenyl)propane-2,2 also known as bisphenol-A, 0.62 g. (4.4 mmol.) of 2,2,6,6,N-pentamethylpiperidine, 0.06 g. (0.20 mmol.) of palladium(II)dibromide, 0.30 g. (0.60 mmol.) to manganese(II)bis(benzoinoxime), 4 g. of molecular sieve Type 3A and 30 ml. of methylene chloride. Carbon monoxide and air were passed through the solution for 42 hours. Reverse phase liquid chromatography showed the presence of bisphenol-A and bisphenol-A dimers, trimers, pentamers and higher oligomers. An additional 0.06 g. (0.20 mmol.) of palladium(II)dibromide was added and the reaction continued. The $\overline{M}_n$ number average molecular weight of the polycarbonate was estimated at 2,800 with about a 10% recovery. This example demonstrates and utility of my catalytic process in the preparation of polycarbonates of bisphenol-A.

While not wishing to limit my invention to any theory, it is believed that the practice of my invention is significantly improved by the presence of molecular sieves because of the ability of the molecular sieves to selectively absorb carbon dioxide and water as opposed to carbon monoxide oxygen and hydrogen.

In the practice of my process, the Group VIIIB elements, after separation from the resulting reaction products can be oxidized or reduced by any means to any oxidation state, and can be re-employed, that is recycled, in the aromatic process described herein.

Although the above examples have illustrated various modifications and changes that can be made in the carrying out of my process, it will be apparent to those skilled in the art that other Group VIIIB metals, phenolic compounds, ligands, oxidants, redox components, drying agents, phase transfer agents and solvents as well as other reaction conditions can be effected without departing from the scope of the invention.

I claim:

1. An aromatic carbonate process which comprises contacting under substantially anhydrous reaction conditions, a phenol, carbon monoxide, a base, a Group VIIIB element selected from ruthenium, rhodium, palladium, osmium, iridium or platinum, and an oxidant having an oxidation potential greater than that of the said selected Group VIIIB element.

2. The claim 1 process, wherein said Group VIIIB element is present in an ionic form.

3. The claim 1 process, wherein said base is a tertiary amine.

4. The claim 1 process, wherein said Group VIIIB element is associated with a carbonyl group.

5. The claim 1 process, wherein said Group VIIIB element is associated with a halide.

6. The claim 1 process, wherein said Group VIIIB element is coordinated with a ligand selected from an arsine, a stibine, a phosphine, a nitrile or a halide.

7. The claim 1 process, wherein said Group VIIIB element is associated with an inorganic halide compound.

8. The claim 1 process, furher comprising separating at least a portion of resulting aromatic carbonate product.

9. The claim 1 process, further comprising a drying agent.

10. The claim 1 process, further comprising a manganese or a cobalt redox co-catalyst.

11. The claim 10 process, wherein the phenol is p-cumylphenol, the base is 2,2,6,6,N-pentamethylpiperidine, the redox co-catalyst is bis(benzoinoxime)manganese(II), the oxidant is air, the Group VIIIB element is palladium dibromide, and further comprising a molecular sieve drying agent.

12. The claim 1 process, wherein the Group VIIIB element is palladium.

13. The claim 10 process, wherein the phenol is bis(4-hydroxyphenyl)propane-2,2, the base is 2,2,6,6,N-pentamethylpiperidine, the redox co-catalyst is bis(benzoinoxime)manganese(II), the oxidant is oxygen, the Group VIIIB element is palladium(II)dibromide, and further comprising a molecular sieve drying agent.

14. The claim 10 process, wherein the phenol is phenol, the base is 2,2,6,6,N-pentamethylpiperidine, the redox co-catalyst is bis(benzoinoxime)manganese(II), the oxidant is oxygen, the Group VIIIB element is palladium(II)dibromide, and further comprising a molecular sieve drying agent.

15. The claim 10 process, wherein the redox co-catalyst is a cobalt chelate complex of the formula

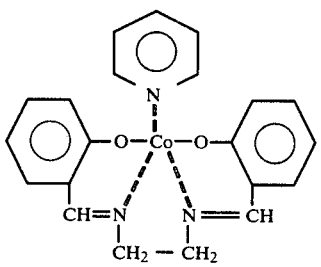

16. An aromatic polycarbonate process which comprises contacting under substantially anhydrous reaction conditions an aromatic polyphenol with carbon monoxide, a base, a Group VIIIB element selected from the class consisting of ruthenium, rhodium, palladium, osmium, iridium and platinum, and an oxidant having an oxidation potential greater than that of the said selected Group VIIIB element.

17. An aromatic polycarbonate process which comprises contacting under substantially anhydrous reaction conditions an aromatic bisphenol of the formula:

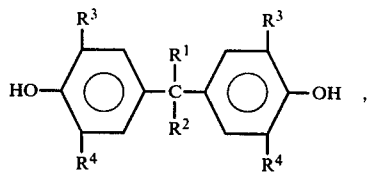

where independently each $R^1$ and $R^2$ is hydrogen, $C_{1-4}$ alkyl or phenyl and independently each $R^3$ and $R^4$ is hydrogen or $C_{1-4}$ alkyl, with carbon monoxide, a Group VIIIB element selected from the class consisting of ruthenium, rhodium, palladium, osmium, iridium and platinum and an oxidant having an oxidation potential greater than that of the said selected Group VIIIB element.

18. The claim 17 process, wherein $R^1$ and $R^2$ are methyl and at least on of $R^3$ and $R^4$ is hydrogen.

19. The claim 18 process, wherein the base is a tertiary amine.

20. The claim 19 process, carried out in the presence of an inert solvent.

21. An aromatic polycarbonate process which comprises contacting under substantially anhydrous reaction conditions on aromatic bisphenol of the formula:

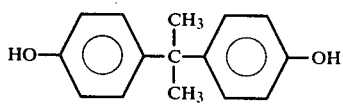

with carbon monoxide, a base, a Group VIIIB metal selected from the class consisting of ruthenium, rhodium, palladium, osmium, iridium and platinum, and an oxidant having an oxidation potential greater than that of the said selected Group VIIIB element.

22. An aromatic monocarbonate process which comprises contacting under substantially anhydrous reaction conditions an aromatic phenol of the formula:

wherein $R_a$ represents an aromatic radical wherein the —OH radical is attached directly to an aromatic ring carbon atom and x is the number 1, with carbon monoxide, a base, a Group VIIIB element selected from the class consisting of ruthenium, rhodium, palladium, osmium, iridium and platinum, and an oxidant having an oxidation potential greater than that of the said selected Group VIIIB element.

23. The claim 22 process, wherein $R_a$ is selected from carbo- or heteromonocyclic, polycyclic or fused polycyclic radicals.

24. The claim 23 process, wherein the base is a tertiary amine.

25. The claim 24 process, carried out in the presence of an inert solvent.

26. An aromatic monocarbonate process which comprises contacting under substantially anhydrous reaction conditions a phenol with carbon monoxide, a base, a Group VIIIB element selected from the class consisting of ruthenium, rhodium, palladium, osmium, iridium and platinum, and an oxidant having an oxidation potential greater than that of the said selected Group VIIIB element.

27. The claim 1 process further comprising a phase transfer agent.

28. The claim 27 process further comprising a manganese redox co-catalyst.

29. The claim 28 process wherein said base is an alkali or alkaline earth metal base, said phase transfer agent is an onium halide, and said redox co-catalyst in a manganese diketone.

30. The claim 29 process wherein said base is sodium hydroxide, said phase transfer agent is tetrabutylphosphonium bromide, and said oxidant is manganese(II)bis-(acetoacetonate).

31. The claim 16 process further comprising a phase transfer agent.

32. The claim 31 process further comprising a manganese redox co-catalyst.

33. The claim 32 process wherein said base is an alkali or alkaline earth metal base, said phase transfer agent is an onium halide, and said redox co-catalyst is a manganese diketonate.

34. The claim 33 process wherein said base is sodium hydroxide, said phase transfer agent is tetrabutylphosphonium bromide, and said redox co-catalyst is manganese(II)bis(acetoacetonate).

35. The claim 17 process further comprising a phase transfer agent.

36. The claim 35 process further comprising a manganese redox co-catalyst.

37. The claim 36 process wherein said base is an alkali or alkaline earth metal base, said phase transfer agent is an onium halide, and said redox co-catalyst is a manganese diketonate.

38. The claim 37 process wherein said base is sodium hydroxide, said phase transfer agent is tetrabutylphosphonium bromide, and said redox co-catalyst is manganese(II)bis(acetoacetonate).

39. The claim 21 process further comprising a phase transfer agent.

40. The claim 39 process further comprising a manganese-redox co-catalyst.

41. The claim 40 process wherein said base is an alkali or alkaline earth metal base, said phase transfer agent is an onium halide, and said redox co-catalyst is a manganese diketonate.

42. The claim 41 process wherein said base is sodium hydroxide, said phase transfer agent is tetrabutylphosphonium bromide, and said redox co-catalyst is manganese(II)bisacetoacetonate).

43. The claim 22 process further comprising a phase transfer agent.

44. The claim 43 process further comprising a manganese redox co-catalyst.

45. The claim 44 process wherein said base is an alkali or alkaline earth metal base, said phase transfer agent is an onium halide, said said redox co-catalyst is a manganese diketonate.

46. The claim 45 process wherein said base is sodium hydroxide, said phase transfer agent is tetrabutyphosphonium bromide, and said oxidant is manganese(II)bis(acetoacetonate).

47. The claim 26 process further comprising a phase transfer agent.

48. The claim 47 process further comprising a manganese redox co-catalyst.

49. The claim 48 process wherein said base is an alkali or alkaline earth metal base, said phase transfer agent is an onium halide, and said redox co-catalyst is a manganese diketonate.

50. The claim 49 process wherein said base is sodium hydroxide, said phase transfer agent is tetrabutylphosphonium bromide, and said redox co-catalyst is manganese(II)bis(acetoacetonate).

51. The claim 30 process further comprising a molecular sieve.

52. The claim 34 process further comprising a molecular sieve.

53. The claim 38 process further comprising a molecular sieve.

54. The claim 42 process further comprising a molecular sieve.

55. The chain 46 process further comprising a molecular sieve.

56. The claim 50 process further comprising a molecular sieve.

* * * * *